US010672288B2

(12) United States Patent
Ribeira et al.

(10) Patent No.: US 10,672,288 B2
(45) Date of Patent: Jun. 2, 2020

(54) AUGMENTED AND VIRTUAL REALITY SIMULATOR FOR PROFESSIONAL AND EDUCATIONAL TRAINING

(71) Applicant: SimX, Inc., Mountain View, CA (US)

(72) Inventors: Ryan Joseph Ribeira, Mountain View, CA (US); Karthik Venkataraman Sarma, Los Angeles, CA (US); Stanley Thomas Stadelman, Jr., Livermore, CA (US); Srihari Kumar Namperumal, Belmont, CA (US); Jason Robert Ribeira, Castro Valley, CA (US); Christopher Ryan Miller, Tempe, AZ (US)

(73) Assignee: SimX, Inc., Mountain View, CA (US)

( * ) Notice: Subject to any disclaimer, the term of this patent is extended or adjusted under 35 U.S.C. 154(b) by 342 days.

(21) Appl. No.: 15/452,108

(22) Filed: Mar. 7, 2017

(65) Prior Publication Data

US 2017/0213473 A1 Jul. 27, 2017

Related U.S. Application Data

(63) Continuation of application No. PCT/US2015/049021, filed on Sep. 8, 2015.

(60) Provisional application No. 62/047,589, filed on Sep. 8, 2014.

(51) Int. Cl.
*G09B 19/00* (2006.01)
*G09B 9/00* (2006.01)
*G06T 19/00* (2011.01)
*G06F 19/00* (2018.01)
(Continued)

(52) U.S. Cl.
CPC ............... *G09B 9/00* (2013.01); *G06F 3/011* (2013.01); *G06F 19/3456* (2013.01);
(Continued)

(58) Field of Classification Search
CPC .......... G09B 9/00; G09B 23/30; B25J 9/1689; G06F 19/3456; G06F 19/3481; G06K 9/00342; G06T 11/60; G06N 3/008
See application file for complete search history.

(56) References Cited

U.S. PATENT DOCUMENTS 8,382,485 B2 * 2/2013 Bardsley ............... G09B 23/30
434/262
8,647,124 B2 * 2/2014 Bardsley ............... G09B 23/30
434/262
(Continued)

*Primary Examiner* — Jerry-Daryl Fletcher
*Assistant Examiner* — Daniel E Lane
(74) *Attorney, Agent, or Firm* — Invoke

(57) ABSTRACT

A method and apparatus for an augmented reality simulator for professional and educational training is provided. The simulator provides a training environment spanning one or more physical locations in which one or more virtual avatars representing purely virtual objects or persons or real physical objects or persons which are located at a different physical location are projected into the physical space. The avatars are interactive with other avatars and real objects or persons and update over time or in response to actions taken by other real or virtual elements, or based on predefined instructions. Sensors and devices are used to detect the locations of and actions taken by real persons or real objects and this sensed data is used to evolve the state of the simulation and avatars based on predefined instructions and programs and update the view of all participants.

20 Claims, 9 Drawing Sheets

(51) Int. Cl.
  *G09B 5/10*   (2006.01)
  *G09B 5/06*   (2006.01)
  *G09B 23/28*  (2006.01)
  *G06F 3/01*   (2006.01)
  *G06K 9/00*   (2006.01)
  *G06T 11/60*  (2006.01)
  *G06T 13/40*  (2011.01)
  *G09B 23/30*  (2006.01)
  *G09B 25/02*  (2006.01)

(52) U.S. Cl.
  CPC ..... *G06F 19/3481* (2013.01); *G06K 9/00342* (2013.01); *G06T 11/60* (2013.01); *G06T 13/40* (2013.01); *G06T 19/00* (2013.01); *G09B 5/06* (2013.01); *G09B 5/10* (2013.01); *G09B 23/28* (2013.01); *G09B 23/30* (2013.01); *G09B 25/02* (2013.01); *G05B 2219/32014* (2013.01)

(56) References Cited

U.S. PATENT DOCUMENTS

| | | | | |
|---|---|---|---|---|
| 2003/0156143 A1* | 8/2003 | Westenskow | ....... | G06F 19/3456 715/848 |
| 2009/0112538 A1* | 4/2009 | Anderson | ............ | G06Q 10/06 703/6 |
| 2011/0159469 A1* | 6/2011 | Hwang | .................. | A61B 5/222 434/247 |
| 2011/0216060 A1* | 9/2011 | Weising | ................... | G09G 5/08 345/419 |
| 2011/0248995 A1* | 10/2011 | Vaughan | ................. | G06K 9/44 345/420 |
| 2012/0154557 A1 | 6/2012 | Perez et al. | | |
| 2013/0078598 A1* | 3/2013 | Dunne | .................. | G09B 19/00 434/128 |
| 2013/0257877 A1* | 10/2013 | Davis | ...................... | A63F 13/12 345/473 |
| 2013/0293468 A1* | 11/2013 | Perez | ...................... | G06F 3/033 345/158 |
| 2014/0065588 A1* | 3/2014 | Jacobson | ............ | G09B 23/283 434/263 |
| 2014/0147820 A1* | 5/2014 | Snow | .................. | G06F 19/3481 434/247 |
| 2014/0164037 A1* | 6/2014 | Rao | ...................... | G06Q 30/0207 705/7.13 |
| 2015/0017623 A1* | 1/2015 | Ceruti | ................. | G06F 19/3481 434/258 |
| 2015/0262016 A1* | 9/2015 | Rothblatt | ............. | A61B 5/0476 348/77 |
| 2016/0346612 A1* | 12/2016 | Rowley | ................ | A43B 3/0005 |

* cited by examiner

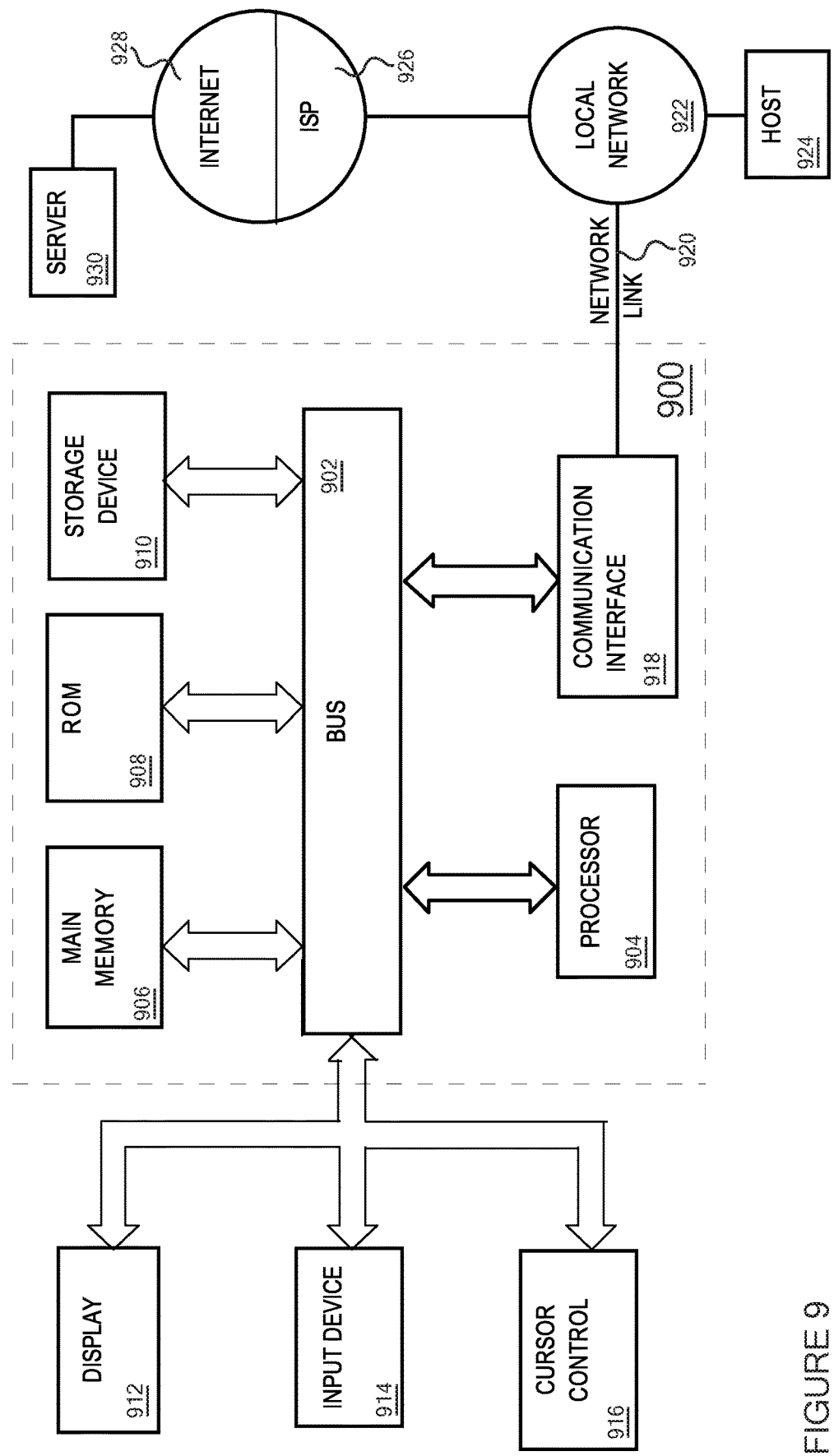

AUGMENTED AND VIRTUAL REALITY SIMULATOR FOR PROFESSIONAL AND EDUCATIONAL TRAINING

CROSS-REFERENCE TO RELATED APPLICATIONS; BENEFIT CLAIM

This application is a continuation of International Application No. PCT/US2015/049021, filed Sep. 8, 2015, which claims the benefit of Provisional Appln. No. 62/047,589, filed Sep. 8, 2014, the entire contents for both of which are hereby incorporated by reference as if fully set forth herein.

FIELD OF THE DISCLOSURE

The present disclosure relates to computer-based training utilizing simulation, and more specifically to augmented reality simulation software for professional and educational training purposes, including but not limited to medical and mechanical training.

BACKGROUND

The concept of simulation of critical events to hone skills, in contrast to mere practice, has long been a staple of human training methodology. At its heart, the goal of simulation is to truly mimic the physical and psychological experience of an event, thus harnessing the power of emotional context and psychological stress to retain both physical and intellectual skills and lessons with more reliability than practice alone can yield.

Various industries have adopted and refined simulation-based training methodologies, attempting to replicate work environments as precisely and accurately as possible to prepare students and professionals for critical events that may be encountered in practice. In the aviation industry, for example, flight simulators have improved over time as computer technology has become more advanced and affordable. In the institution of medicine, medical scenario simulation has grown to become a standard component of medical training and continuing education, typically relying on physical "dummy" apparatuses to represent the "patients" or "subjects" of the simulation.

Simulation-based training systems that are both low cost and completely immersive are significantly limited or non-existent in many industries. Further, current simulation tools are not tightly integrated with computer systems that allow for simulation case scenarios to be authored for distribution and reuse, or stored and aggregated for analysis, scoring, and review. With regard to medicine specifically, the majority of simulation taking place in medical education today involves the use of full-scale, computer-driven manikins that are capable of portraying human physiology and around which a realistic clinical environment can be recreated. In this sense, manikin simulators are uniquely suited for training scenarios capable of satisfying the requirements for equipment fidelity, environment fidelity, and psychological fidelity, or the capacity to evoke emotions in trainees that they could expect to experience in actual practice. However, there remains a gap in the manikin's ability to represent a broad array of demographics or visually important clinical scenarios. In addition, there are significant logistical challenges associated with gathering work-hour limited trainees at sufficiently frequent intervals to foster maintenance of clinical competency using manikin simulation. Instructor salaries, technician salaries, and opportunity-costs involved in equipping and maintaining a state-of-the-art simulation facility employing such manikins represents a significant cost and places significant limitations on the ability of manikin simulation to integrate fully into existing curricula.

Beyond the training of novice medical staff, simulation-based training has also come to be recognized as integral to maintaining skills of fully licensed and practicing medical staff, but the logistical challenges of bringing staff together outside of regularly scheduled hours to a high fidelity environment or of bringing a high fidelity environment to the regular work location of the staff has presented an almost insurmountable challenge to simulation-based training in this population. The cost and lack of portability of the modern high fidelity medical simulation system also presents a barrier to its wider adoption outside of medical education institutions and outside of wealthy nations, despite the clear need for such maintenance training within community institutions and novice and maintenance training in developing countries. The limited ability of manikin based systems to represent different ethnicities, age groups, and visual symptoms, including rashes, also represents a degradation of psychological fidelity, with these aspects of medical simulation particularly relevant to training of experienced providers and in the field of tropical medicine.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

Exemplary embodiments of the present invention described below with detailed descriptions and accompanying drawings. Embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

FIG. 9 is a diagram illustrating the use of one or more special-purpose computing devices.

DETAILED DESCRIPTION

Figure 1:
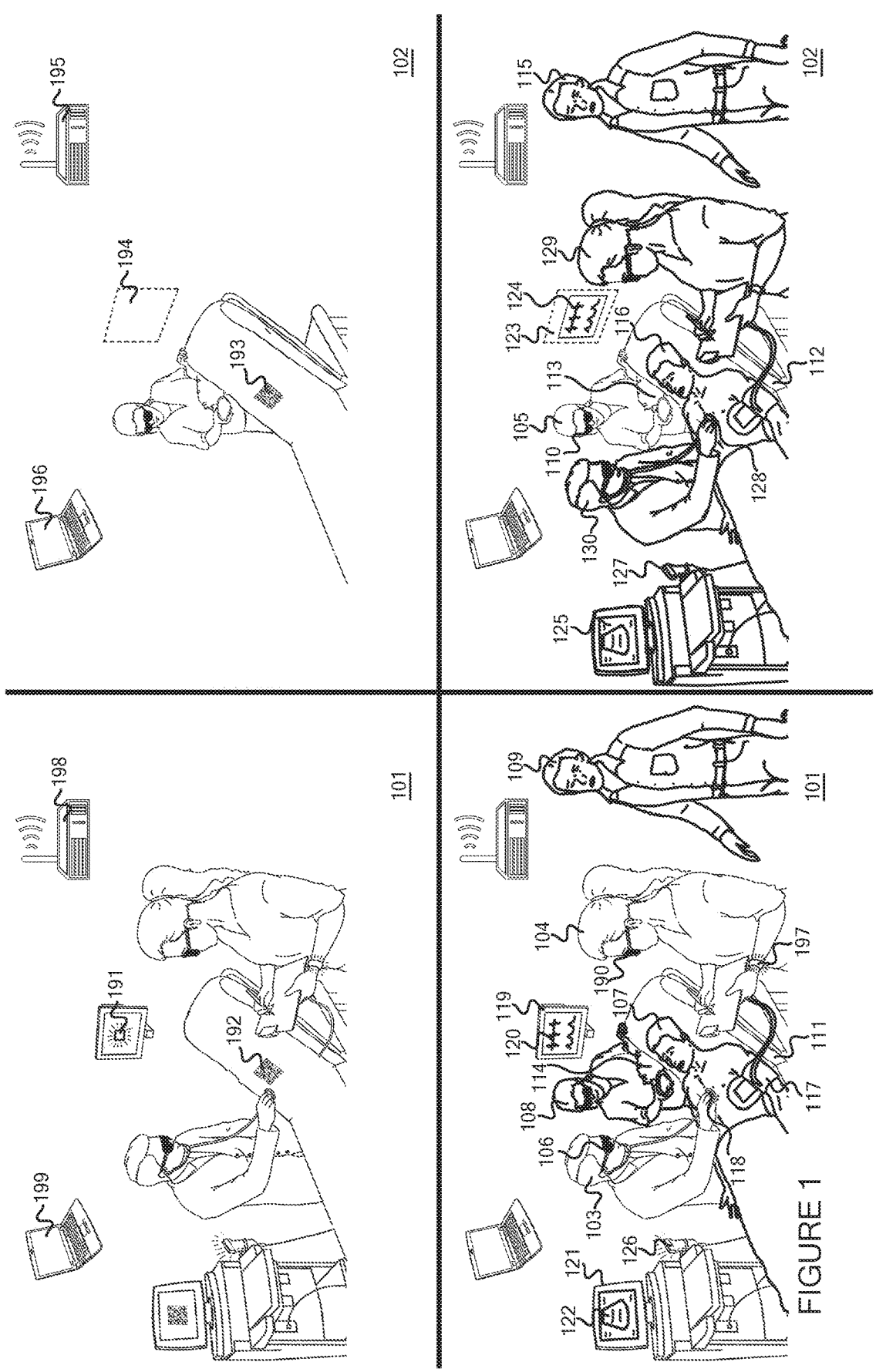
FIG. 1 is a diagram illustrating the use of a shared augmented reality environment for medical training over multiple geographic locations.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Techniques are described herein that provide for systems, methods, and non-transitory computer-readable media for simulation based training. This methodology uses augmented reality, a particular incarnation of virtual reality, in order to greatly advance the degree of equipment fidelity, environment fidelity, and psychological fidelity available in simulation for training, with certain embodiments also decreasing the cost and improving portability of simulation systems, depending on the particular hardware utilized to realize the simulation system.

Here, an augmented reality environment refers to the perception of a user of their real, physical environment with the addition of virtual, projected, two or three dimensional objects in that environment. Integral to the concept of an augmented reality environment is the feature of the virtual objects to be perceived to exist in the real space as if they were real objects, with the ability of users to walk around them and see them from different angles, as appropriate. In harnessing this for training, the method described enables a replication of nearly an infinite number of environments.

In some embodiments, processes are described herein for establishing an augmented reality environment, utilizing a computer application to author simulation scenario cases, processing actions on virtual objects, and recording the events transpiring while users are immersed in the augmented reality environment. Such scenario cases may be comprised of instruction sets and associated metadata and subordinate instruction sets and data, such as audio data or image data, and may be distributed locally or broadly through the use of an internet infrastructure, marketplace, or other distribution mechanism.

Establishing an augmented reality environment within a real space refers to using computer generated virtual models, or virtual avatars, projected into the space, where the avatars behave as if they are physically in the space, and where multiple users can see each other, or at least placeholders of each other, and the avatars, and interact with the avatars and each other, mimicking a situation where all avatars and users are physically in the real space and are solid objects or beings, even in the scenario where the user themselves are not in the same real space. Virtual avatars may be projected into empty physical locations or they may be projected over existing real objects and partially or fully obstruct the actual view of the real object while allowing for physical interactions, such as touch, with the real object, and allowing for such interactions to be detected and the virtual avatar updated based on the interaction.

Utilizing a computer application to author scenario cases refers to the use of an authoring application which outputs an instruction set that defines the appearance, properties, and behavior of virtual avatars in an augmented reality environment with respect to time, as well as defining virtual avatars' effects on other objects in the augmented reality and the effect of other objects on the virtual avatar.

Processing the actions on virtual objects in an augmented reality environment refers to the method of matching virtual versions of real objects to the real objects in the augmented reality environment using sensors, where the virtual object occupies the same space as the real object, and using the actions and interactions between these virtual objects to accurately change the appearance or other properties of the virtual objects as defined by their pre-programmed properties. This also refers to the method of changing the appearance or properties of purely virtual objects, with no physical analog in the real environment, based upon actions and interactions with other purely virtual objects or real objects, as defined by their pre-programmed properties. This could include purely visual changes, movements, or other properties such as audio vocalizations. Detection of actions and interactions may involve the use of wearable or freestanding sensors, such as cameras, IR beacons, wireless beacons, and inertial measurement units. Some sensors may be attached to augmented reality devices worn by participants, or they may be attached to real objects and communicate with the system to provide additional information about the state of the real and virtual space relative to those objects, or they may be freestanding.

Recording the events transpiring in an augmented reality environment refers to a method of detecting and recording user actions such as body movement, and speech in addition to the passage of time, the visual or audio experience of participants, and the occurrence of pre-programmed events, and using that record to evaluate user performance based up on pre-determined metrics.

FIG. 1 shows one possible embodiment of using a shared augmented reality environment for training, in which a plurality of real participants and real objects are located in distinct geographic spaces, with the shared augmented reality environment populated by virtual avatars of living beings and inanimate objects. Specifically, the figure shown represents the use of the shared augmented reality environment for medical training in two locations, depicted here utilizing four panels, showing one medical training session occurring simultaneously (or near simultaneously due to potential lag caused by network and/or different processing speeds of devices) at two different physical locations 101 and 102. The figure shown depicts the real physical spaces in locations 101 and 102 in the top two panels, populated only by real physical objects and living beings. The bottom two panels of the figure depict the augmented reality environment, populated by real physical objects and living beings as well as virtual avatars of objects and beings. The figure depicts location 101 on the left half of the figure and location 102 on the right half of the figure.

According to this particular embodiment, three human participants including a physician 103, a nurse 104, and a respiratory therapist 105, are participating in a medical training session concurrently. Participants 103 and 104 are located in one particular physical location 101 depicted in the scene, and participant 105 is located in a different physical location 102 depicted in the scene.

The physician 103 is wearing an augmented reality device 106, which is a device that has the capability to display to the surrounding physical space with virtual elements projected into the space which appear to be physically present within that space, immersing the wearer in the augmented reality environment, and which also, in this embodiment, has further capabilities built into the device or attached to the device in a modular fashion. Specifically, the embodiment shown includes internet communication, sensors, including multiple cameras, IR tracking devices, inertial measurement units, and other sensors, audio speaker systems, and headphones. Further, one embodiment of device 106 may include the capability of binocular vision to further immerse the participant in the augmented reality environment.

The physician's augmented reality device 106 is projecting three virtual avatars 107, 108, and 109, which are computer generated virtual representations of living beings which are not physically present, but which are projected into the physical view of the individual wearing an augmented reality device so as to appear to be physically present, which may be animated and interactive with the physical participants and with other virtual avatars, and which may experience changes of state during the course of use of the system.

The virtual avatar 108 is the representation of human participant nurse 105, who is not physically present in the physical location 101 where physician 103 is located, but who is instead using the system in a different location 102 and is being physically projected into physician 103's field of view by the augmented reality device 106 in a position and orientation relative to the marker 192 affixed to bed 111 in location 101 that corresponds to participant 105's position and orientation in location 102 relative to the marker 193 affixed to bed 112. In this embodiment, markers 192 and 193 are visibly distinct patterns, quick response codes. When the marker is read by the simulation system, the marker pattern, or in other embodiments the other unique qualities about the marker, are compared to a pre-programmed set of markers for that simulation session. Once the matching marker is found in the reference set, the data for the avatar programmed to be projected over that marker is retrieved and used to project the avatar in three dimensions over the marker. The appropriate position and orientation of the avatar is calculated by the system in part using the sensor data provided by participant 105's augmented reality device 110 as well as participant 103's augmented reality device 106 based on the position and orientation of the marker. The system uses this sensor data to compute the appropriate angles based on the relative position and orientation of the participants in the session to that of an anchor object such as markers 192 and 193 affixed to beds 111 and 112, respectively. Avatar 108 may appear as an exact three dimensional replica of participant 105, or a generic human avatar that occupies the same relative position as participant 105, or a different placeholder graphical avatar located in the same relative position.

Alternatively, this position and orientation may be computed based on relative positioning and orientation to any other physical object or marker in the scene, where a marker is a pre-planned physical object, visual or physical pattern, or electromagnetic emitter used as a fiduciary point by the system to perform relative position and orientation calculations, or the position and orientation may be computed using a different methodology, such as simultaneous localization and mapping, as needed. An example of a physical pattern, a flat wall, is shown with virtual marker 194, which represents the placement of a location anchor, the virtual marker 194, within the augmented reality environment based upon pattern recognition of a flat surface, where the two-dimensional virtual avatar, cardiac monitor screen 124, is located relative to virtual marker 194. An example of an electromagnetic marker, a marker embedded into ultrasound probe 126, is also shown, where such an electromagnetic marker may communicate location, orientation, and identity data, similar to the visual markers 192 and 193. In this case, the marker also allows for the registration of the real US probe 126 with its virtual avatar 127. In the case of an electromagnetic marker, detailed identity data about the real object to which it is attached, including data regarding how the real object interacts with virtual objects, and data regarding how the virtual object to which it is registered, in this case virtual ultrasound probe 127, should appear and interact may be actively transmitted. In the case of a passive electromagnetic marker that acts similarly to a visual marker, with simulation system sensors only able to read location, orientation, and identity data, the system would use identity data, such as a code being broadcast by the marker, to properly register the correct virtual avatar to the real object. By comparing that identity data sensed to a pre-programmed set of identifiers, the simulation system determines which particular avatar, with its corresponding properties, is to be projected to overlay the marker, in this case avatar 127. Once the virtual avatar is registered to the physical object, the system projects the avatar over the marker as pre-programmed, typically occupying the identical space as the real object and following the movement of the real object in the augmented reality space exactly. Thus, when real object 126 is registered and interacts with virtual objects, such as avatar 107, the simulation system uses pre-programmed instructions to determine the result of the interaction. For instance, placing real object 126 in contact of the chest of avatar 107 in the augmented reality space would also place virtual object 127 in contact with the chest of avatar 107, which can be detected by the system as a collision, and which can trigger the display of US result image 122 on device 121. This collision is also recorded by the system, and if listed as a performance metric, the use of probe 126 by participants may contribute to their performance score. In one embodiment, not depicted in the figure explicitly, additional sensors, such as cameras not attached to any participants, or three-dimensional location systems may also be used to calculate positions and orientations of visual or electromagnetic markers.

As indicated above, actions of participants, avatars, and/or other objects within the augmented reality environment may be monitored and recorded. Such monitoring may be useful in the context of evaluating the performance of one or more participants that are engaged in a training simulation. Using at least one sensor, such as a microphone, camera, etc., an augmented reality device may detect an occurrence of an action within the augmented reality space. The action that is detected may vary from implementation and may include, without limitation, a physical movement of a participant, a vocalization by a participant, an interaction between a participant and a virtual avatar, an interaction between two different virtual avatars, an interaction between a physical object and a virtual avatar, an interaction between a participant and a physical object, or some combination thereof. Once detected, the occurrence of the action may be recorded to volatile or non-volatile storage of a computing device. The data used to record the action may vary and may include without limitation, text data describing the action, a visual image of the action, a transcription of a vocalization, or some combination thereof. During the simulation or at the end of the simulation, the recorded action may be compared to a performance metric. In some embodiments, the performance metric identifies a set of goal action, where the goal actions specify the actions a participant should take or, in some instances, the actions a participant should not take, during the simulation. There may be grades or weights associated with the different goal actions. For instance, if a participants takes the best course of action, the participant may receive the highest performance score for that action whereas a different action may be an appropriate action, but not the best, where the participant earns a lower performance score for this action, and the lowest performance score if no appropriate action was taken. The system may thus compare records of the action to the performance metric to perform an evaluation of the performance of one or more participants. The system then generates a performance evaluation that includes one or more measures that indicate the performance of the one or more participants in the augmented reality environment. A measure may be a score, grade, or some other quantitative or qualitative indicator of a participants performance, the calculation of which may vary from implementation to implementation and may depend on the performance metric used and the actions recorded during the simulation. In the context of a medical simulation, the system may monitor whether a participant orders medication, whether the dosage used/applied is correct, whether the participant performs a surgical procedure on a virtual avatar correctly, response times between events and actions, etc. to evaluate the performance of the participant. The evaluation report may be printed, stored, and/or transmitted over a network to notify the participant and/or a moderator of the simulation result.

The virtual avatar 108 mimics the physical actions performed by participant 105 in location 102. In this scene, participant 105 is using tool 113, a bag-valve-mask. The bag-valve-mask is projected virtually into the space 101 as virtual tool 114 using the system. The use of tool 113 is detected by augmented reality device 110 by means of the sensors on the device 110 and the physical configuration of tool 113, or alternatively by the use of a fiduciary marker placed upon tool 113, or by some other marking technique as previously described. The system detects the use of tool 113 by participant 105 and projects virtual tool 114 with avatar 108 so that her actions in location 102 are seen by the other participants, mimicking a situation in which participant 105 is using tool 113 in the same physical space 101 as participants 103 and 104. The virtual avatar 129 similarly mimics the physical actions performed by participant 104 in location 101. In this case, emitter 197 provides additional location data regarding the location of participant 104's wrist, allowing her body movements to be detected with higher precision and avatar 129 to more accurately mirror her body movements.

In this embodiment, the augmented reality medical training session in which the three real individuals 103, 104, and 105 are participating has been designed and created using an authoring application whose output was a file containing the information necessary to project the virtual avatars present in in the shared augmented reality environment. This output file contains an instruction set that describe the physical properties of the virtual avatars, including their appearance, as well as different sets of properties unique to each different avatar.

In the figure, avatars 107 and 109 in location 101 represent human beings, where the instruction set within the file contains data for the devices 106, 110, and 190 to project those avatars. Further, as avatars 107 and 109 do represent human beings, the instructions describing them also provide information regarding their physiology and behavior, how that physiology and behavior vary over time as the instructions are executed, and how their physiology, behavior, and appearance may change in response to different interactions with real objects, virtual avatars, and virtual interventions, such as medication administration. Avatar 114 in location 101 represents a tool, and the instruction set also contains data on the appearance and properties of this tool, including how its use affects other virtual avatars.

The computing device 199 and the router 198 in location 101 act as a host and conduit for network communications, respectively, allowing the coordinated projection of all of the avatars in the augmented reality environment. In this case, the computing device 199 is running a simulation execution application which can execute the previously mentioned instruction set to build the augmented reality environment. Computing device 199 communicates wirelessly, in this case, with client devices 106, 110, and 190, as well as the emitters contained within objects 118, 126, and 191, either directly or via routers 198 and 195.

As the host, computer device 199 receives location data and property data on all markers from sensing devices, and then rebroadcasts that data to all projection devices in order to allow for a coordinated and simultaneous (or near simultaneous) view of all avatars and to change the augmented reality environment appropriately in response to avatar interactions. In this way, all three dimensional avatars correctly occupy the three dimensional augmented reality space for all participants, such that when viewed from different angles and positions the avatars occupy a consistently same space in a consistently same orientation as if they were physically present. Given sufficient computing power, device 106 or 190 may also function as the host. In the context of internet access via routers 198 and 195, devices 199, 106, 110, and 190 may also download data as needed from a remote server in addition to accessing local databases in order to project all the avatars populating the shared augmented reality environment over the course of a simulation session.

Host device 199 may also be used by any participant to enter commands during the execution of an instruction set that change the augmented reality environment, for instance creating a new avatar or triggering a change in physiology in a human avatar. Control of the simulation environment using the host device 199 running the simulation execution application also includes navigation of the instruction set describing the augmented reality environment, so that if a participant must leave the simulation environment, wishes to re-experience a specific event, or wishes to skip ahead to a later time point, execution of the instruction set can be appropriately navigated.

The virtual avatar 109 represents a virtual character that does not represent a physical human participant. This character is generated entirely by the system, and can interact with the human participants as well as other virtual avatars. Avatar 109 is projected into the physician 103's view by device 106 and appears to be in the same physical space 101 as physician 103. The same virtual character is projected into physical space 102 by augmented reality device 110 and seen by nurse 105 as avatar 115. Avatars 115 and 109 are both representations of the same system generated virtual character, and are projected similarly in both locations 101 and 102. The actions and interactions of this character are projected into the view of all of the participants in the simulation and dictated by the instruction set being executed by device 199.

The virtual avatar 107 also represents a virtual character that does not represent a physical human participant. In this scene, avatar 107 represents a patient, who is also represented in location 102 as avatar 116. Avatar 107 is projected to appear on top of physical bed 111 and avatar 116 is projected to appear on top of physical bed 112 in order to provide a realistic patient setting for the purpose of the represented medical training session. The virtual patient is fully simulated by the system and is interactive with other participants as well as virtual avatars based upon the instruction set being executed by device 199. The physiological and physical state of the virtual patient is calculated and simulated by the system based on accepted physiological parameters as well as the pre-programmed parameters of the associated training scenario. The simulated parameters may include breathing and respiratory rate, heart rate, oxygen saturation, auscultated sounds, ultrasound images and other imaging modalities, physical signs and stigmata, and other physiologic parameters as appropriate. The simulated patient may also converse with other participants and avatars or communicate in other verbal or nonverbal means. Using a sensor, the system may detect vocalization by the participants as well the content of those vocalizations, which may comprise a command to the system, for instance to administer a medication, or an interaction with a virtual avatar, such as a question about the virtual patient's medical history. The simulated state of the patient may evolve over time or due to events such as actions taken by other virtual avatars or physical participants.

The virtual patient avatar 107 can be interacted with directly using body parts of the participant or using tools, either virtual, such as tool 117, or physical, such as tools 118, 113, and 126. Physical tools that are present in only one location such as 113, 118, and 126, can be projected into another, as are virtual tools 114, 128, and 127 respectively. The results of tool use can be projected onto a real screen such as results 120 on screen 119, or they can be projected onto a virtual screen, such as virtual results 124 on virtual screen 123. In this case, results 120 and 124 represent the same results, which are projected simultaneously and identically in both locations 101 and 102, using real screen 119 and virtual screen 123, respectively. Results from a specialized tool such as ultrasound 126 that require a specialized machine to display, such as machine 121, can be projected onto the real screen as on machine 121, or a virtual machine can be projected into the space if no real machine is present, as is virtual machine 125 in physical location 102.

Results from the use of real or virtual tools upon virtual avatars are computed by the system. The use of tools is detected by the system using appropriate sensors. In this scene, physician 103's use of stethoscope tool 118 is detected by his augmented reality device 106 by use of a wireless beacon on device 118. Alternatively, this tool use could be detected by use of sensors on device 106 such as a camera detecting a fiduciary marker placed on tool 118 or the recognition of the physical shape of tool 118. The fact that the tool 118 is currently interacting with avatar 107 is detected by the system by means of correlating the virtual simulated spatial position of avatar 107 and the physical location of tool 118 and the virtual tool 128 to which it is registered. The system then outputs the appropriate result in the appropriate manner. In the case of stethoscope tool 118, which is placed over the simulated tricuspid auscultatory area of patient 107, the appropriate heart sound is played by device 106 and heard seamlessly by participant 103 in a manner similar to that if participant 103 was using his device upon a real physical human patient. In this scenario, the virtual patient 107 also has chest wall tenderness, where placement of the stethoscope 118 upon his chest triggers the virtual patient 107 to groan, as per the instruction set being executed and controlling the augmented reality environment.

The use of therapeutic tools, such as bag valve mask tool 113 is similarly processed by the system. The system detects the use of the tool by an appropriate mechanism such as those discussed above. When the tool is used upon the patient, an appropriate physiological response is calculated based on the current simulated physiological and physical state of the patient and the characteristics of the specific tool, which may be automatically assigned to virtual avatar of the tool based upon the tool's identity, the patient's state is updated based on this calculation, and then the projection of the patient and any physiological or physical signs and results are updated accordingly. In this scenario, participant 105 uses tool 113, a bag-valve-mask, to provide blow-by oxygen. In response to the presence of tool 113 near virtual patient 116's face, virtual patient 116 in location 102 has slower breathing, which is mirrored simultaneously by virtual patient 107 in location 101, with the breathing changes and improved oxygenation, reflected by a higher oxygen saturation percentage, displayed simultaneously on virtual monitors 120 and 124.

In location 102, physical participant 105 sees a similar scene to that seen by participant 103 in location 101 even though participant 105 is in a different physical location. This is effected by participant 105's augmented reality device 110, which projects physical participants 103 and 104 as virtual avatars 129, 130 respectively. Avatars 129 and 130 are projected to appear in the same relative position to physical bed 112 and marker 193 as physical participants 103 and 104 are relative to physical bed 111 and marker 192. Alternatively, positioning could be accomplished through a different mechanism, such as those described above. Additionally, virtual avatars 115 and 116 are projected into location 102 just as avatars 109 and 107 are projected into location 101 respectively. Virtual screen 123, and virtual machine 125 are also projected into location 102 in order to duplicate physical screen 119 and physical machine 121 so that participant 105 is able to see all of the results seen by participants 103 and 104. This overall provides the appearance to participants 103, 104, and 105 that they are located in the same room and interacting with the same patient 107 and virtual character 109 even though in fact they are in two separate locations 101 and 102. The participants are further able to interact as a team and perform their duties with the patient together seamlessly providing an integrated training experience.

Figure 2:
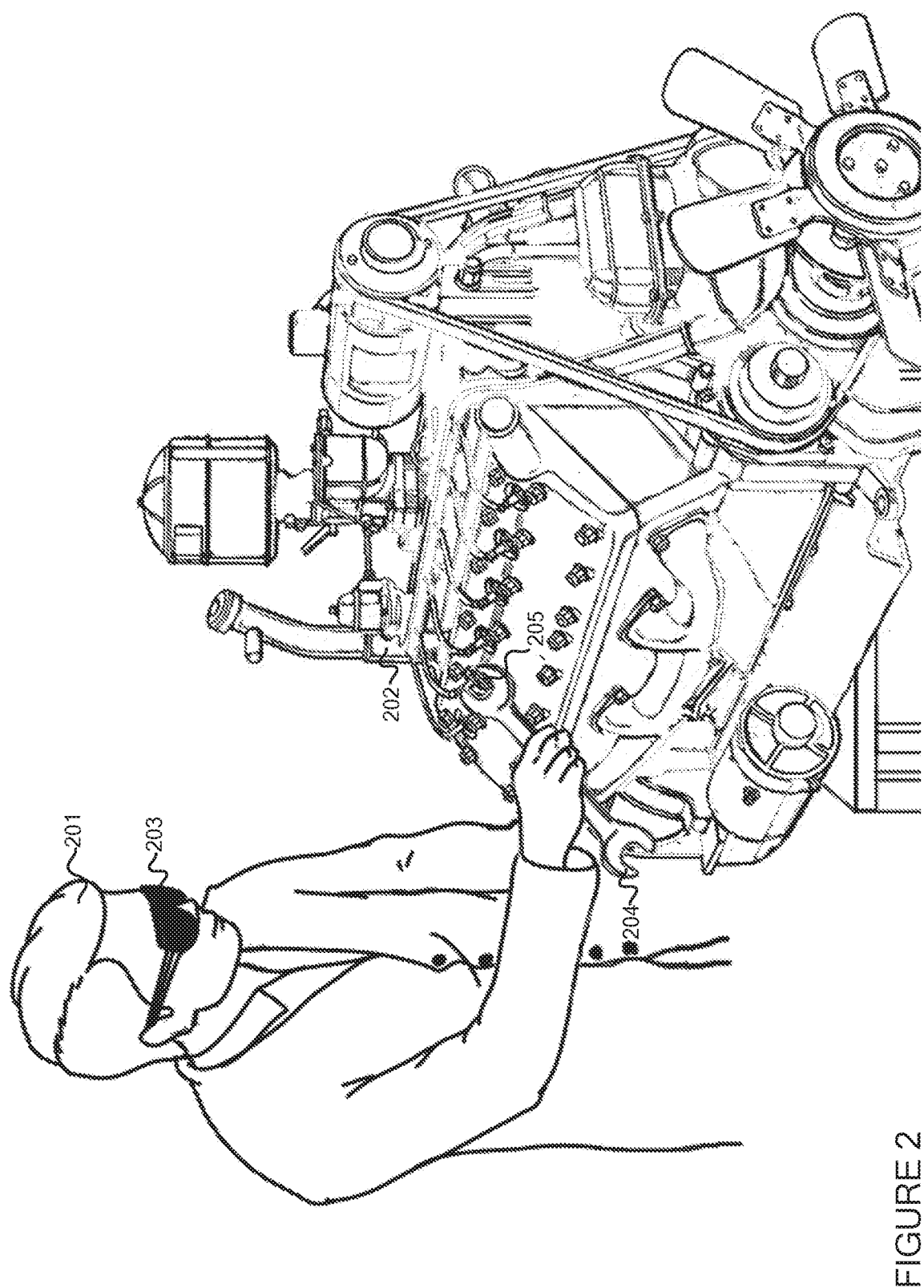
FIG. 2 is a diagram illustrating the use of an augmented reality environment for automotive training.

FIG. 2 shows one possible embodiment of using an augmented reality environment for training, in which a single real participant, mechanic 201, uses the augmented reality environment for mechanical training in a single location, with a virtual training apparatus, engine 202, projected virtually into the physical space using augmented reality device 203.

The mechanic 201 is wearing an augmented reality device 203. The embodiment shown includes interne communication, sensors, including multiple cameras, IR tracking devices, inertial measurement units, and other sensors, audio speaker systems, and headphones in addition to the augmented reality capability of the device.

The augmented reality device 203 is projecting virtual avatar 202, which is a computer generated virtual representation of an engine which is not physically present, but which is projected into the physical view of mechanic 201 by augmented reality device 203 so as to appear to be physically present, and which is animated and interactive with both physical participants and other virtual avatars, and which may experience changes of state during the course of use of the system.

In this embodiment, the augmented reality mechanical training session in which mechanic 201 is participating has been designed and created using an authoring application whose output was a file containing the information necessary to project the virtual engine avatar 202 present in the augmented reality environment as well as an instruction set describing the physical and interactive properties of the virtual engine avatar.

Avatar 202 represents a computer virtual representation of a simulated engine, where the instruction set within the file contains data for device 203 to project the avatar 202 into the view of mechanic 201. Further, this instruction set also describes how the simulated engine is affected by interactions with mechanic 201, such as mechanic 201's use of tool 204 to make a modification of the engine. This includes both physical instructions which will affect the visual appearance of avatar 202 as well as instructions that describe how this modification will affect the operation of the engine, which will update the internal representation of the simulated engine, thus allowing for further modifications and operations to be performed upon the engine with composited effects, and which may allow the simulation environment to predict the performance characteristics of the modified engine for simulated testing or for evaluation of mechanic 201's performance in the training session.

Tool 204 represents a physical tool being held by mechanic 201. The sensors of augmented reality device 203 detect the use of tool 204 and its identity. In this embodiment, the camera of device 203 detects the physical form of tool 204 and uses this information to determine the position of tool 204 relative to the position of mechanic 201 and the virtual simulated position of engine 202. In the figure, physical tool 204 intersects with engine avatar 202 at point 205, which corresponds to a sub-component of virtual engine avatar 202. Using the sensed information from augmented reality device 203, the simulation system detects that mechanic 201 is attempting to interact with engine avatar 202 using tool 204 at point 205, and using the file instructions, determines what effect the interaction performed by mechanic 201 will have upon the simulated engine based upon the identity of tool 204 and the tool properties contained within the instruction set or downloaded by the simulation application as prompted by the instruction set. The system makes the appropriate modification to the simulated appearance of engine 202, and this updated appearance is projected to mechanic 201 via augmented reality device 203. This provides the appearance to mechanic 201 that the use of tool 204 is modifying avatar 202 just as it would modify a real engine if used at the same point, providing the appearance that mechanic 201 is interacting with a real engine. The modifications made by mechanic 201 are saved to the instruction set file and make the modifications persistent after they are complete.

After mechanic 201 is finished making modifications to avatar 202 using tool 204, he may run a simulated test of the virtual engine. The simulation system then uses the saved modifications to calculate the appropriate performance of the modified engine using the file instructions and then projects an avatar of the engine in operation, allowing mechanic 201 to evaluate the changes that he has made. Alternatively, mechanic 201 may request an evaluation of his performance in the training scenario. The simulation system would compare the modifications made by mechanic 201 and the resulting performance to preset parameters contained in the instruction set file and then provide a score and explanation to mechanic 201.

Figure 3:
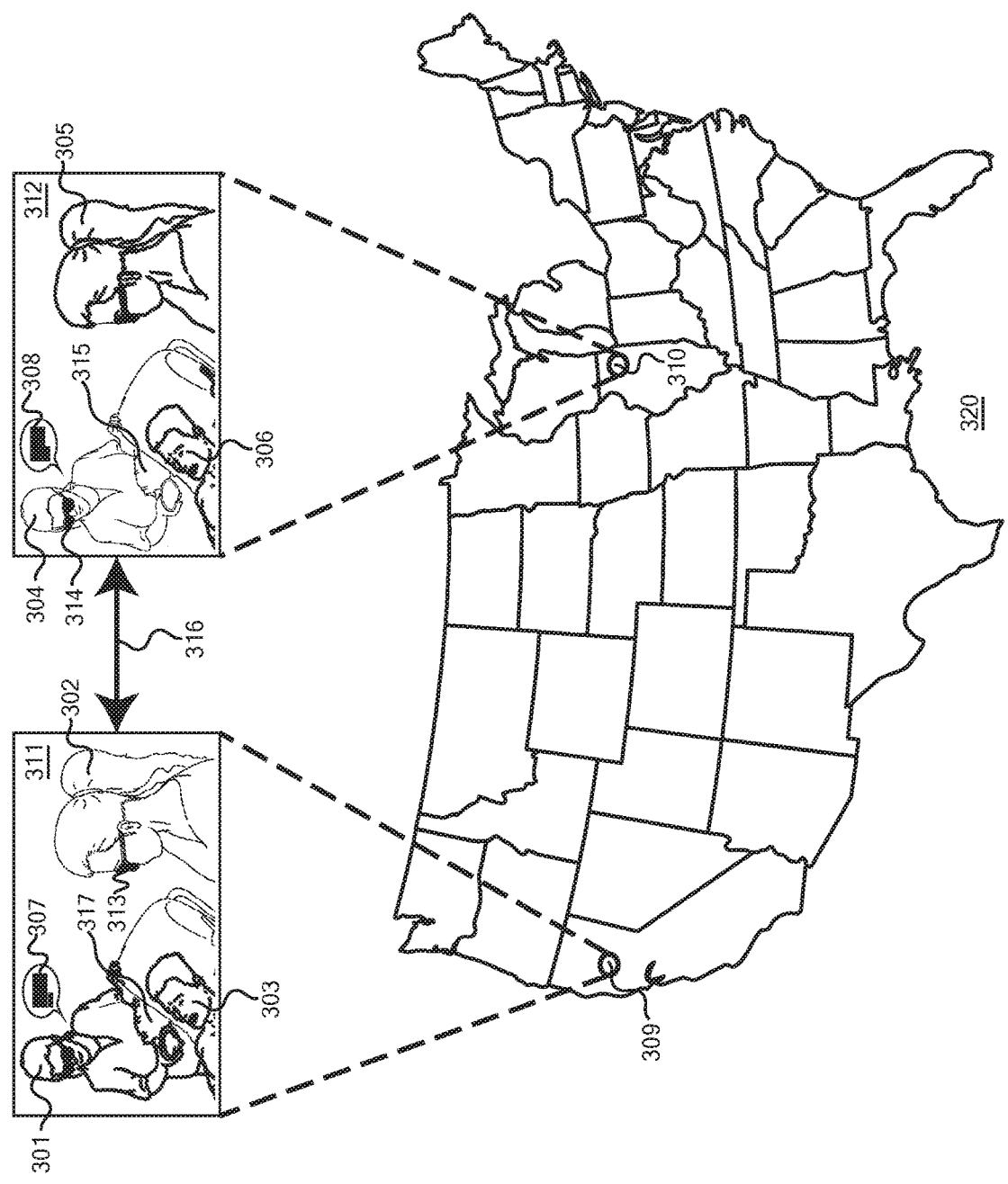
FIG. 3 is a diagram illustrating the use of a shared augmented reality environment for training over multiple geographic locations and the communications between those locations.

FIG. 3 shows one possible embodiment of using a shared augmented reality environment for training, in which a plurality of real participants and real objects are located in distinct geographic spaces, with the shared augmented reality environment populated by virtual avatars of living beings and inanimate objects. Specifically, the figure shown represents the use of the shared augmented reality environment for medical training in two locations, depicted here utilizing two panels 311 and 312 overlaid over map 320 which depicts distinct training locations 309 and 310. Panel 311 represents a view of the training session at location 309, and panel 312 represents a view of the training session at location 310.

According to this particular embodiment, two human participants including respiratory therapist 304 and nurse 302 are participating in a medical training session concurrently. Participant 302 is located at physical location 309 and participant 304 is located at physical location 310. Both participants 302 and 304 are participating in the same shared medical training session concurrently, though from different physical locations.

Participants 302 and 304 are wearing augmented reality devices 313 and 314, respectively. In this embodiment, these devices provide, in addition to augmented reality projection capability, internet communication, sensors, including multiple cameras, IR tracking devices, inertial measurement units, and other sensors, audio speaker systems, and headphones attached to the device in a modular fashion or built into the device.

Avatars 303 and 306 represent virtual patient avatars which both represent the same simulated patient. The virtual patient is fully simulated by the system and is interactive with other participants as well as virtual avatars based upon the instruction set being executed by the system. Avatar 303 is being projected by device 313 into the view of participant 302, and avatar 306 is being projected by device 314 into the view of participant 304. Both avatars appear the same and react the same way, as they are representing the same underlying simulated patient. Interactions occurring at either location upon either avatar are reflected by both the avatar at the location where the interaction is physically located as well as the avatar at the other location. This is facilitated by internet communication. In this figure, participant 304 is preparing to use bag valve mask 315 on avatar 306. The use of this tool is detected by sensors on device 314. Device 314 also detects the relative spatial position of participant 304 to patient avatar 306. This set of information is then broadcast over the internet, represented by arrow 316, from location 310, to device 313 at location 309. This transmission occurs directly between the two devices, or is relayed through an internet server, or a series of internet servers and other devices, and may first be processed and transformed by a series of internet servers and other devices before arriving at its destination. The resulting information is then used by device 313 to project virtual avatar 301, which represents participant 304 and is located at the same location relative to virtual patient avatar 303 as the physical participant 304 is relative to virtual patient avatar 306, into the physical space observed by participant 302.

Similarly, device 313 detects participant 302's location relative to patient avatar 303. This information is transmitted over the internet from location 309 to location 310, directly, or via an internet server, or a series of internet servers and other devices. This information may first be processed and transformed by a series of internet servers and other devices before arriving at its destination. The resulting information is then used by device 314 to project virtual avatar 305, representing participant 302, into the physical space observed by participant 304. This transmission occurs near-instantaneously, allowing for actions taking by participants 304 or 302 to be observed nearly immediately by the other participant, providing the experience that both participants are working in the same space, even though they are located in two distinct physical locations that are geographically separated. In addition, non-human objects like tools 315 may also be captured and projected as necessary, so that both participants see the same set of objects, either due to the presence of a real object or a virtual avatar representing that real object, such as virtual tool avatar 317.

Also in this particular embodiment, participant 304 is currently speaking speech 308. The audio information comprising this speech is recorded by the microphone sensor present in device 314. Alternatively, this information could be recorded by any other audio recording equipment present and connected to the augmented reality system, such as a freestanding microphone with wireless or wired internet connectivity, or a different augmented reality device being worn by a different participant. This information is transmitted from device 314 at location 310 to device 313 at location 309. This transmission occurs directly between the two devices, or is relayed through an internet server, or a series of internet servers and other devices, and may first be processed and transformed by a series of internet servers and other devices before arriving at its destination. Device 313 then uses its headphones to broadcast the audio information to participant 302. Alternatively, any other device connected to the augmented reality system with audio speaker capability could be used to broadcast the audio information, such as a freestanding speaker system with wireless or wired connectivity. This gives the appearance of avatar 301 speaking speech 307 to participant 302 even though the actual physical speech is occurring at a different physical location. The content of speech 308 is also analyzed by device 314 or another device running a simulation execution application enabling the augmented reality environment, with that content being recognized as a command to the system or other relevant speech, as indicated by the simulation session instruction set. Similarly, other actions by either participant can be recorded by the system and transmitted in order to allow the participant at the other physical location to experience those actions, such as physical movements or interaction with physical objects or virtual avatars. This provides a seamless experience in which participants 302 and 304 appear to experience participating in training at the same location even though they are physically located at two distinct physical locations.

Figure 4:
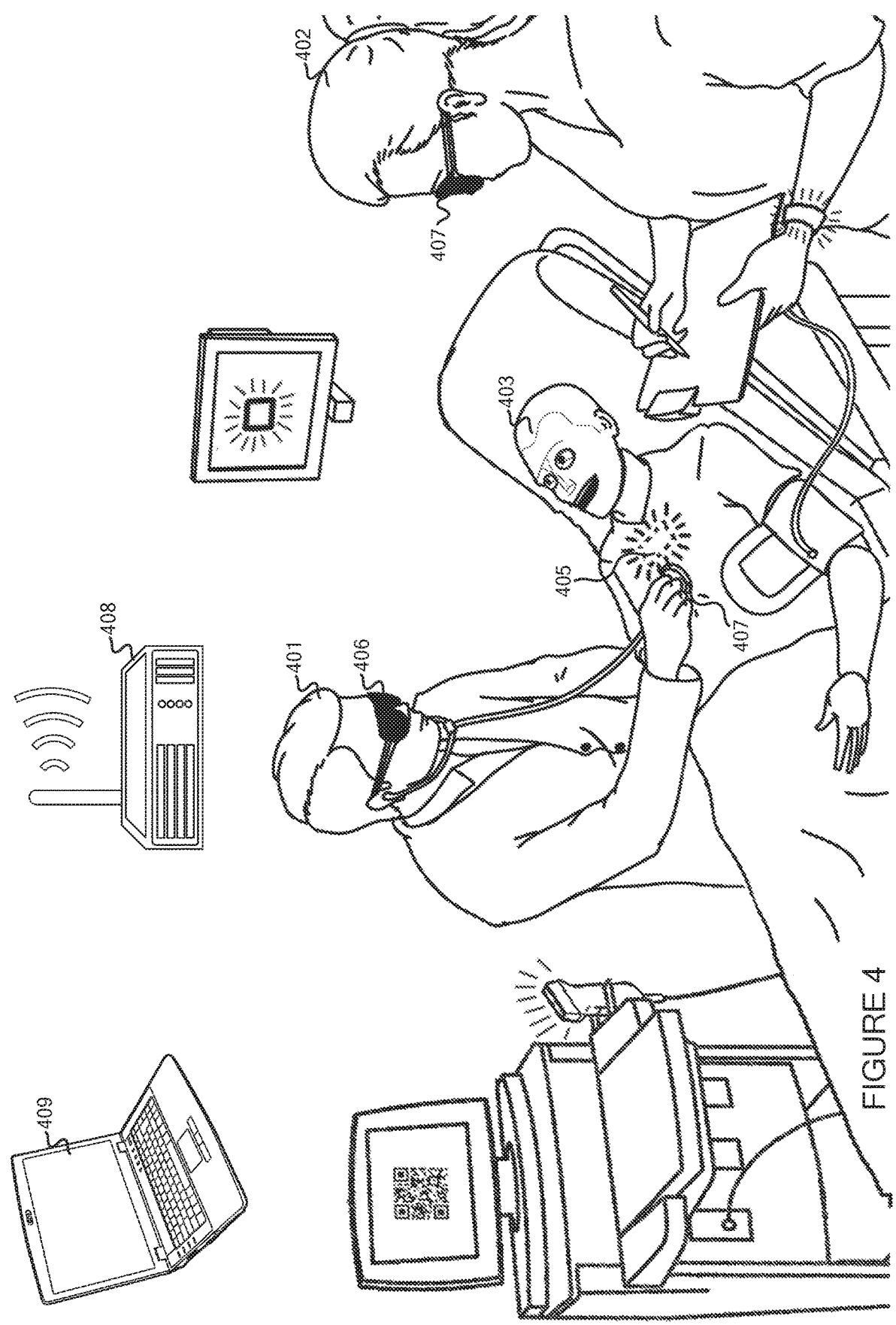
FIG. 4 is a diagram illustrating the use of a shared augmented reality environment for training using a physical dummy as a point of reference to anchor the augmented reality environment.

FIG. 4 shows one possible embodiment of using a shared augmented reality environment for training. Specifically, the figure shown represents the use of the shared augmented reality environment for medical training by two real human participants, physician 401 and nurse 402. Participants 401 and 402 are wearing augmented reality devices 406 and 407 respectively, which in this embodiment in addition to possessing augmented reality projection capability, includes interne communication, sensors, including multiple cameras, wireless beacon tracking sensors, and other sensors, and headphones built into the device or attached in a modular fashion to the device.

According to this particular embodiment, a physical patient dummy 403 is being used for the simulation. The physical dummy 403 physically contains device 405, which is a combined sensor, wireless receiver, and wireless transmitter, further acting as a trackable wireless beacon for the dummy 403. Device 405 is able to communicate with augmented reality devices 406 and 407, which use the information from the device to track the relative position of dummy 403 to participants 401 and 402 respectively. This allows devices 406 and 407 to project a realistic virtual patient avatar into the perception of participants 401 and 402 over the physical location of dummy 403, providing the illusion that the virtual patient avatar is in the physical location actually occupied by dummy 403. In addition, devices 406 and 407 transmit the data from beacon 405 via router 408 to laptop 409 which is running the simulation execution application with the simulated patient.

Physician 401 is currently using real stethoscope tool 407 on what he perceives to be the virtual patient avatar, which is projected over the real physical location of dummy 403. Since dummy 403 is in the same location, physician 401 receives the tactile sensation caused by the contact between tool 407 and dummy 403. In addition, device 406 detects using its sensors that physician 401 is using stethoscope 407 on the virtual patient avatar and transmits that information via router 408 to laptop 409. Device 405 also detects this stethoscope use and transmits that data to laptop 409 via router 408. Laptop 409 uses the instruction set for the simulation to determine the appropriate response, which is then transmitted back to devices 406 and 407 via router 408.

Figure 5:
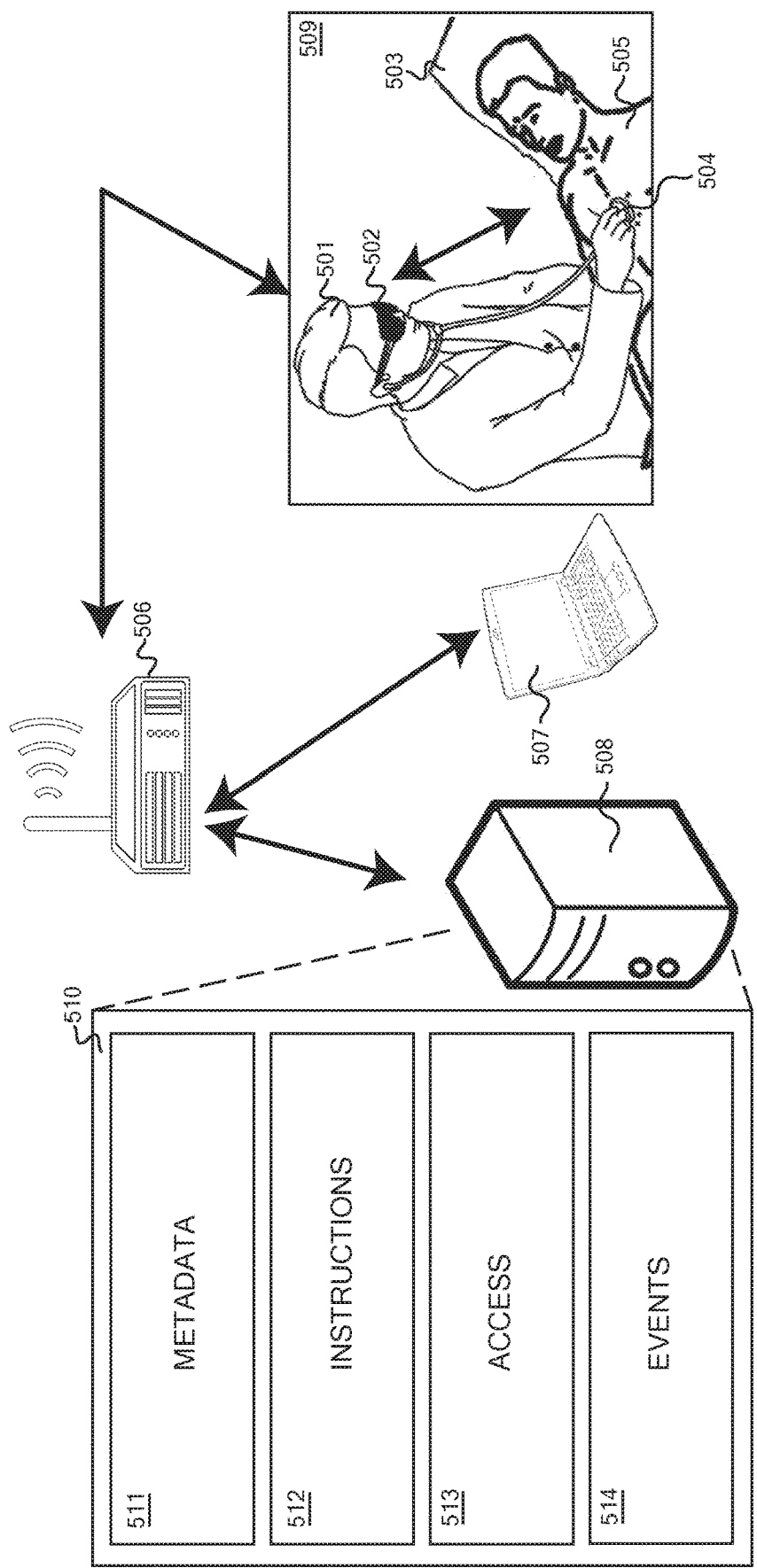
FIG. 5 is a diagram illustrating the use of an augmented reality environment for training, a series of computing devices used to create the environment, and an instruction file specifying the training augmented reality environment.

FIG. 5 shows one possible embodiment of using an augmented reality environment for training. Specifically, the figure depicts one participant, physician 501 using the augmented reality environment for medical training. In addition, several of the computer systems facilitating the augmented reality environment are shown, including network router 506, laptop computer 507, and server 508. In addition, one possible instruction file 510 for this medical training session is graphically represented.

Physician 501 is wearing augmented reality device 502 and is located in location 509. In this embodiment, in addition to augmented reality projection capability, device 502 has further capabilities built into the device or attached to the device in a modular fashion. Specifically, the embodiment shown includes internet communication, sensors, including multiple cameras, IR tracking devices, inertial measurement units, and other sensors, audio speaker systems, and headphones. Virtual patient avatar 505 is being projected into the view of physician 501 by device 502.

In this particular embodiment, instruction file 510 is the instruction file for the medical training session that physician 501 is currently participating in. Instruction file 510 may contain several subcomponents, including those four subcomponents depicted, metadata 511, instructions 512, access rights 513, and event log 514. Instruction file 510 was created by an authoring program which generated the file based on instructions and programming created by the user of the authoring program.

Metadata 511 includes information about the instruction set, which may include a title, type of simulation, number of participants supported, avatar listing, notes for use by individuals running the simulation, and notes for participants.

Instructions 512 includes an instruction set which is used by the augmented reality simulation to control the virtual simulations and avatars and to mediate any interactions in the system. The physical features of avatar 505 are included in this instruction set. Server 508 uses the instructions on these features to generate a three dimensional virtual avatar which is then projected by device 502. Actions of the avatar are also governed by these instructions. For example, the breathing rate of the patient simulation represented by avatar 505 is governed by this instruction set. Server 508, running a simulation execution application, uses these instructions to generate and update the breathing rate of the patient representation, which then updates the animated breathing rate of avatar 505.

Reactions of the avatar to interactions are also specified by the instruction set. As physician 501 uses stethoscope 504 to auscultate patient avatar SOS's tricuspid area, this is detected by the augmented reality device 502 using its sensors, which in this case may include a camera or wireless beacon detector. In this particular embodiment, this is then transmitted to local internet router 506, which relays the information to server 508. Server 508 then uses the instruction set contained in instructions 512 to determine what the reaction should be. For example, the instruction set may specify that the virtual patient should gasp as if it were a real patient being exposed to a cold stethoscope head on bare skin. This would then be relayed by server 508 via router 506 to device 502, which would update avatar 505 to animate it, with the avatar then gasping. In addition, instruction set 512 may specify that the auscultatory heart sound that would be expected from a stethoscope placed over the tricuspid area of a real patient should be heard by the participant using the stethoscope, in this case physician 501. The appropriate sound file as specified by the instruction set would be loaded by server 508, and transmitted to device 502 via router 506. Device 502 would then use its headphone capability to play this audio sound to physician 501. In an alternate embodiment, the sound file would have been transmitted to device 502 at the beginning of the session, and then merely locally accessed when its use was triggered. In addition, instructions 512 may specify that the heart rate of the virtual patient simulation should increase when the stethoscope is used on the patient. Server 508 would then update the heart rate of its internal representation of the virtual patient, and transmit a faster heart sound, as appropriate for the specified heart rate, to be played by device 502 to physician 501. In addition, any associated display of this heart rate, such as a virtual monitor screen, would be updated with the new heart rate.

When physician 501 first begins to use stethoscope tool 504, device 502 may further request information about the tool. This request would be relayed by router 506 to server 508, which would use instructions 512 to determine the nature of the tool. This would then be transmitted back to device 502. Device 502 may then further request all associated audio data in order to cache the data on the device. This request would be transmitted by router 506 to server 508, which would use instructions 512 to determine which files are associated with tool 504. The associated sound files would then be transmitted by server 508 to device 502 in order to reduce future communication time.

Events log 514 contains a log of the events and interactions that occur within this particular execution of the simulation, which in this embodiment is a medical training session. For example, in this embodiment, physician 501's use of a stethoscope over the tricuspid area of virtual patient 505, when transmitted to server 508, is logged and appended to file 510 in area 514 along with any associated metadata of the action, the time of the action, and any appropriate information about the state of the simulation, participants, or virtual avatars or displays, as instructed by instructions 512. This will allow server 508 to use the fact that this event occurred in calculating further evolutions of the state of the simulation if so instructed by the instruction set. This will also allow users to examine the history of past actions that have occurred in this simulation session. In addition, the resulting changes and interactions due to this event as specified by instructions 512 may also be appended to events log 514 if so instructed by instructions 512. This may also allow for server 508 to create a summary and possible grading of the performance of physician 501 at the conclusion of the training session based on a procedure previously created by the author of the instruction file and contained in instruction set 512. At the conclusion of the training session, events log 514 may be copied and saved to serve as a record of the session, or it may be deleted, or it may be otherwise processed for statistical purposes.

In the future, physician 501 may decide after finishing his use of stethoscope 504 to physically adjust the configuration of bed 503 as a medical intervention using his hands. In this embodiment, this action would be detected by the sensors on device 502 or alternatively by sensors or markers on bed 503 or any other external connected sensor, such as a freestanding network enabled camera. This action would be transmitted via router 506 to server 508, where the physician's physical action would be recorded in events log 514, and the appropriate response of the patient simulation would be computed based on instructions 512. The response would then be used to update the patient simulation on server 508, which would then be used to update the patient avatar. The update would then be transmitted to device 502 via router 506.

In this particular embodiment, the simulation session that physician 501 is participating in was previously started by a local training moderator using laptop 507. The moderator accessed a listing of available training sessions on laptop 507. This request was transmitted via router 506 to server 508, which produced a listing of available cases. In order to determine if a case was available for use by the moderator and physician 501, server 508 examines the access rights of a particular instruction file, such as access rights 513 in instruction file 510. Server 508 then compares the access rights contained in the file to the access that the moderator possesses, and if the moderator's access is sufficient to satisfy these access rights, the file is included as an available case in the listing sent to the moderator.

In this particular embodiment, the simulation session that physician 501 is participating in is being concurrently broadcast to laptop 507 for viewing by the training moderator. The training moderator is able to see the scene as seen by physician 501 due to device 502 sensing the scene using its sensors and broadcasting them via router 506 to server 508. In another embodiment, a distinct camera may be present in the physical training environment, with that camera's audio and video data being transmitted via router 506 to server 508. Server 508 then rebroadcasts the scene to laptop 507. In addition, this video information may be appended to events log 514 by server 508 as a record of physician 501's perspective during the training session if so desired. In other possible embodiments, server 508 and laptop 507 may be the same computing device or different computing devices, or a set of computing devices, which may be located in the same location as the participants of the simulation, or in a different location, or in multiple different locations, or distributed using cloud computing. The instruction moderator may be distinct from the participants, or it may be one of the participants, or there may be no moderator. The moderator may be located at the same location as the participants of the simulation, or could be in a remote location. There may be one moderator, multiple moderators, or no moderators. In this scene, the moderator using laptop 507 is also able to make modifications to the current session. For example, the moderator may decide to add an additional sudden medical complication to the training session. This would be entered into laptop 507 and transmitted via router 506 to server 508. Server 508 would use this input in combination with instructions 512 to determine what changes to make to its internal patient representation. These changes would then be used to update the patient avatar and any other virtual avatars or virtual screens, and the results would then be broadcast via router 506 to device 502 and then projected into the view of physician 501.

Figure 6:
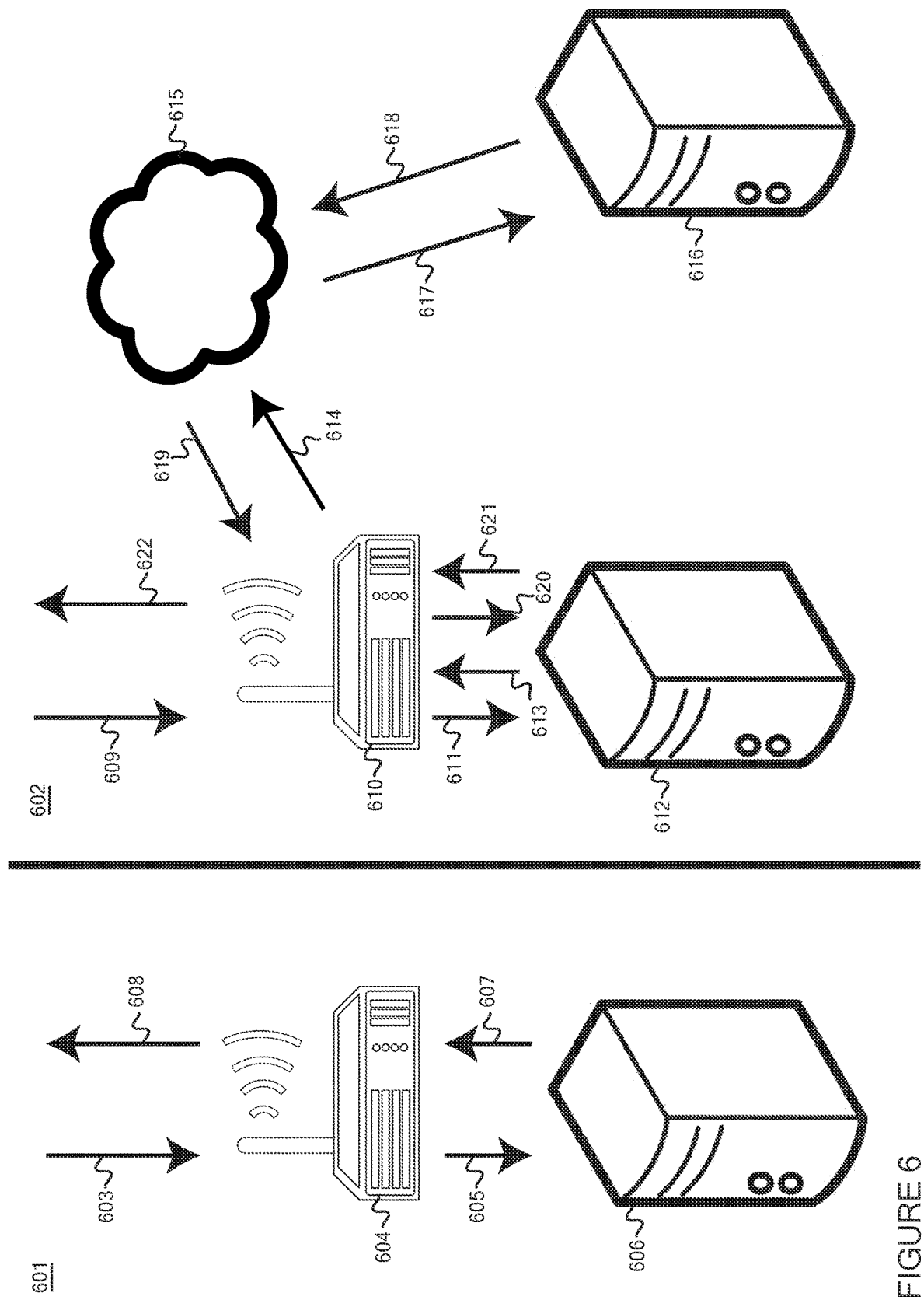
FIG. 6 is a diagram illustrating the use of one or more network computer systems for retrieval of stored instruction files for augmented reality environments, with optional use of a marketplace for instruction files.

FIG. 6 shows one possible embodiment of the infrastructure supporting access to instruction files and associated data by components of the augmented reality environment, including both servers, clients, and other associated computing devices. Two different scenarios are depicted, scenarios 601 and 602.

In the particular embodiment of scenario 601, request 603, which is a request for an instruction file or associated data, such as audio recordings, graphical models, or sub-instruction sets, is transmitted from a client, such as an augmented reality device, a computing device being used by a moderator, or a simulation server, to local router 604. Router 604 then transmits the request as request 605 to local database server 606. In other embodiments, the local database server may be the same computing device as any other device used in the simulation system, such as a moderator client device, or a simulation server, or it may be a distinct computing device, or there may be no local database server. Local database 606 then uses request 605 to search its local datastore and finds the data requested. This data is packaged and transmitted as response 607 to local router 604, which then transmits it as response 608 to the requesting computing device. In other embodiments, there may be additional routers or other networking appliances involved in the communication chain, or the requesting device may be directly networked with the local database server, local database server and the requesting application may be different processes running on the same computing device.

In the particular embodiment of scenario 602, request 609 is also a request for an instruction file or associated data. This request is transmitted to local router 610, which then transmits it as request 611 to local database server 612. Server 612 uses request 611 to search its local datastore, but does not find the data requested. Server 612 then sends request 613 for the data to router 610, which then transmits it via the internet to simulation distribution infrastructure 615 as request 614. This infrastructure may consist of one or more remote computing servers or a cloud computing infrastructure. Infrastructure 615 locates the data request on server 616 and transmits request 617. Server 616 then uses request 617 to search its local datastore and retrieve the requested data, which is then transmitted to infrastructure 615 as response 618. Infrastructure 615 then retransmits the received data as response 619 to router 610, which transmits it as response 620 to local database server 612. Local database server may cache the resulting response data in its local datastore and then retransmits the data as response 621 to local router 610, which retransmits the data as response 622 to the requesting computing device. In other embodiments, multiple routers or other networking appliances may be used in the transmission and retransmission of requests or responses. In other embodiments, server 616 may be a part of infrastructure 615 or may be a standalone server. In other embodiments, local database server 612 may consist of multiple computing devices, all of which search for the data locally before making a request to infrastructure 615, or there may be no local database server at all, in which case the requesting device would transmit request 609 directly to infrastructure 615 via router 610. In other embodiments, response 622 may be processed by the requesting device and as a result additional data may be requested via the same process as request 609. In other embodiments, the request data may be available via an online marketplace accessible via infrastructure 615, in which case information about the data available would be transmitted back to the requestor which would then decide whether or not to purchase the requested data. In one possible such embodiment, the original author of the instruction set or other content may store this content on a local server, such as server 616, and infrastructure 615 would mediate the request for the data by the original server 612, and if a purchase is made, mediate the transfer of valuable consideration from the operators of server 612 to the operators of server 616, and the transfer of the purchased data from server 616 to server 612. In addition, infrastructure 615 may mediate the return of required data, such as metadata regarding use of the content, to server 616. Server 612 may be disallowed from saving the requested content locally, thus requiring a check to be made via infrastructure 615 to ensure that the operators of server 612 continue to have licensing rights to the purchased content and mediating any additional licensing purchases as necessary.

Figure 7:
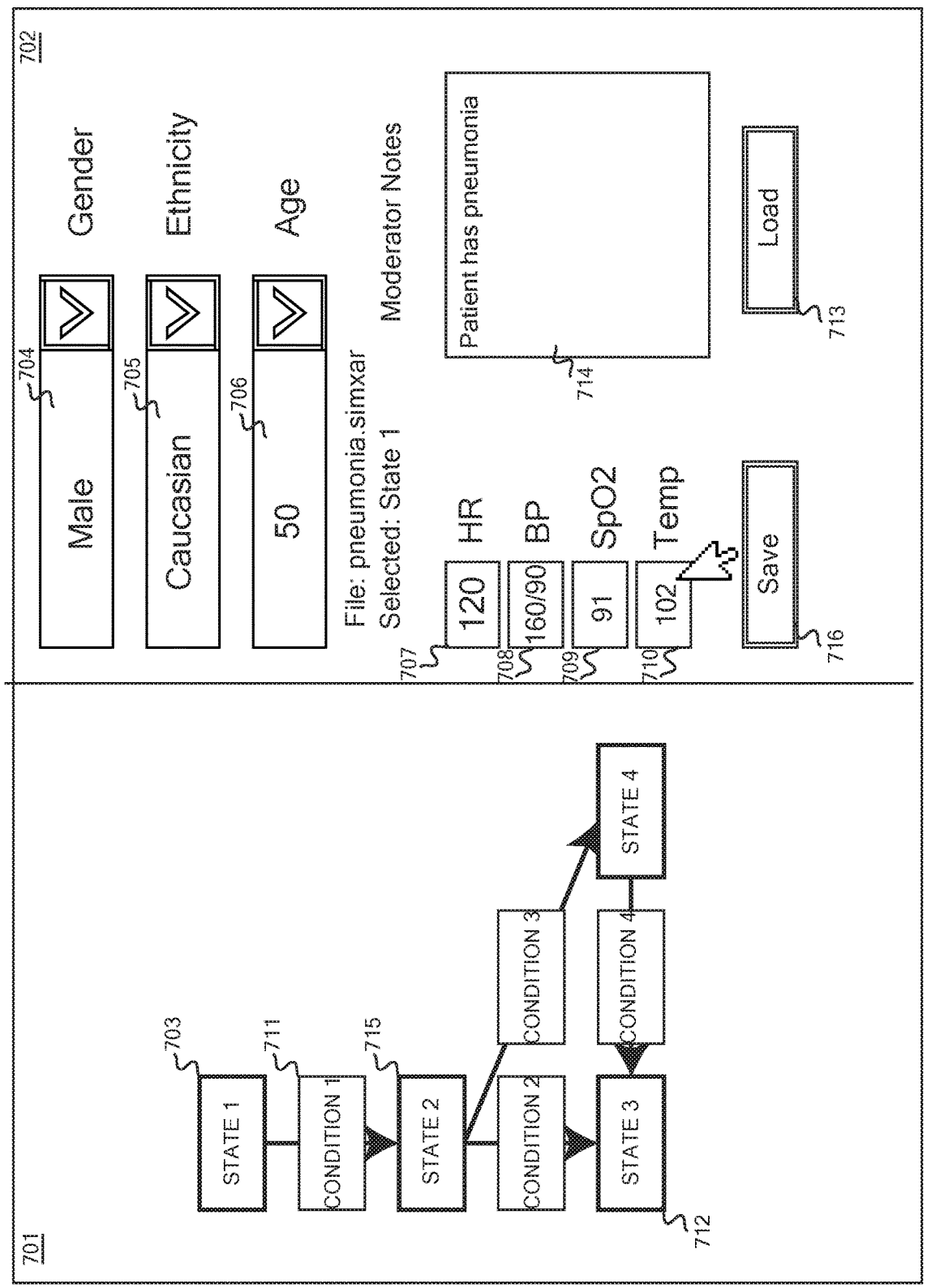
FIG. 7 is a diagram illustrating the use of software for the authoring of instruction files for augmented reality environments.

FIG. 7 shows one possible embodiment of an authoring program for instruction sets used by the augmented reality simulation system. In this embodiment, an author is creating an instruction set for use in a medical training simulation.

In this particular embodiment, a set of states 701 comprising the instruction set has been created by the author. The author is currently editing one particular state 703, some of the parameters for which are displayed on the editing panel 702. The author is able to configure global physical parameters for case, such as the patient's gender 704, ethnicity 705, and age 706 for a virtual patient as may be appropriate in a medical training application of the augmented reality system. In addition, parameters specific to the selected state 703 are configurable, including the physiological variables heart rate 707, blood pressure 708, oxygenation 709 and temperature 710. Additional parameter may also be available to be configured for each state. These parameters could be the same for multiple states, or could be different per state. In addition, free text notes such as 714 may be appended to a state for use by an instruction moderator or participant.

The set of states 701 also includes conditions, such as condition 711. These conditions govern transitions of the simulation from one state to another state. Conditions are also configured by the instruction set author, and could involve any aspect of the simulation, such as the passage of time, interactions by participants and virtual avatars, interactions between virtual avatars, use of real or virtual tools, or any other event in the simulation environment. Conditions may be comprised of a single item or any Boolean configuration of items. When conditions are met, they may cause the transition of the simulation from one state to another state. For example, satisfying condition 711 may cause the simulation state to transition from state 703 to state 715, leading in this example to a change of the physiological characteristics such as the heart rate of the virtual patient with appropriate physical and interactive signs displayed by the virtual avatar representing the patient and on the virtual cardiac monitor displayed in the augmented reality environment.

One state in the set of states 701 may represent an end state or goal state. In this embodiment, state 712 is a goal state defined by the instruction set author. One or more participants in the simulation encoded by the instruction set may be graded based on whether or not this goal state is achieved during the course of the simulation. In addition, failure states can also be added to the set of states which, if reached, end the simulation or rewind the simulation to an earlier state. At the termination of a simulation, the contributions made by individual participants as well as the summated group performance in progressing through the states of the simulation may be used to provide feedback or grading of performance. In addition, factors such as the length of time required to progress between states, incorrect or irrelevant actions or interactions, communications between participants or between participants and virtual avatars, and other events that occur during the course of the simulation may be used in grading and feedback. The procedure for performing this grading and feedback as well as the factors to be considered are part of the instruction set authored by the author using the authoring program. Grading and feedback may be provided to participants directly through the augmented reality system, or a printed or electronic report may be provided. Grading and feedback may be recorded permanently and stored, or it may be deleted, or statistics may be compiled and transmitted to a database for storage and future evaluation. Grading and feedback may be provided for the entire group or on an individual basis to participants.

Instruction set authors may also load other instruction sets, such as by using a load command 713, in order to include other instruction sets within the instruction set being authored, allowing for the reuse or editing of common components or a modular instruction structure. Other data components, such as tool definitions, audio data, or graphics models, may also be loaded into an instruction set. Components may be loaded from instruction sets located on the authoring device, or from an external piece of computer readable media, or from the internet. Components may also be accessible through a marketplace, and authors may be able to purchase reusable components for use within their instruction sets. Loaded components may be integrated into a set of states or other instruction set and may be used in conjunction with newly defined instructions or states.

Instruction sets can be saved locally using a save command 716 allowing for use of the instruction set for simulation session. In addition, instruction sets may be uploaded to a local database server or to an internet storage database for distribution. This database may be part of an instruction set marketplace, and other users may then be able to purchase licenses for use of the instruction set, potentially including use for simulation execution or use as subcomponents for instruction set authoring. Fees may be charged on a per instruction set, per use, or per participant basis. Statistics on the use of the instruction set may be collected and transmitted back to the author for use in future development or for tracking.

Figure 8:
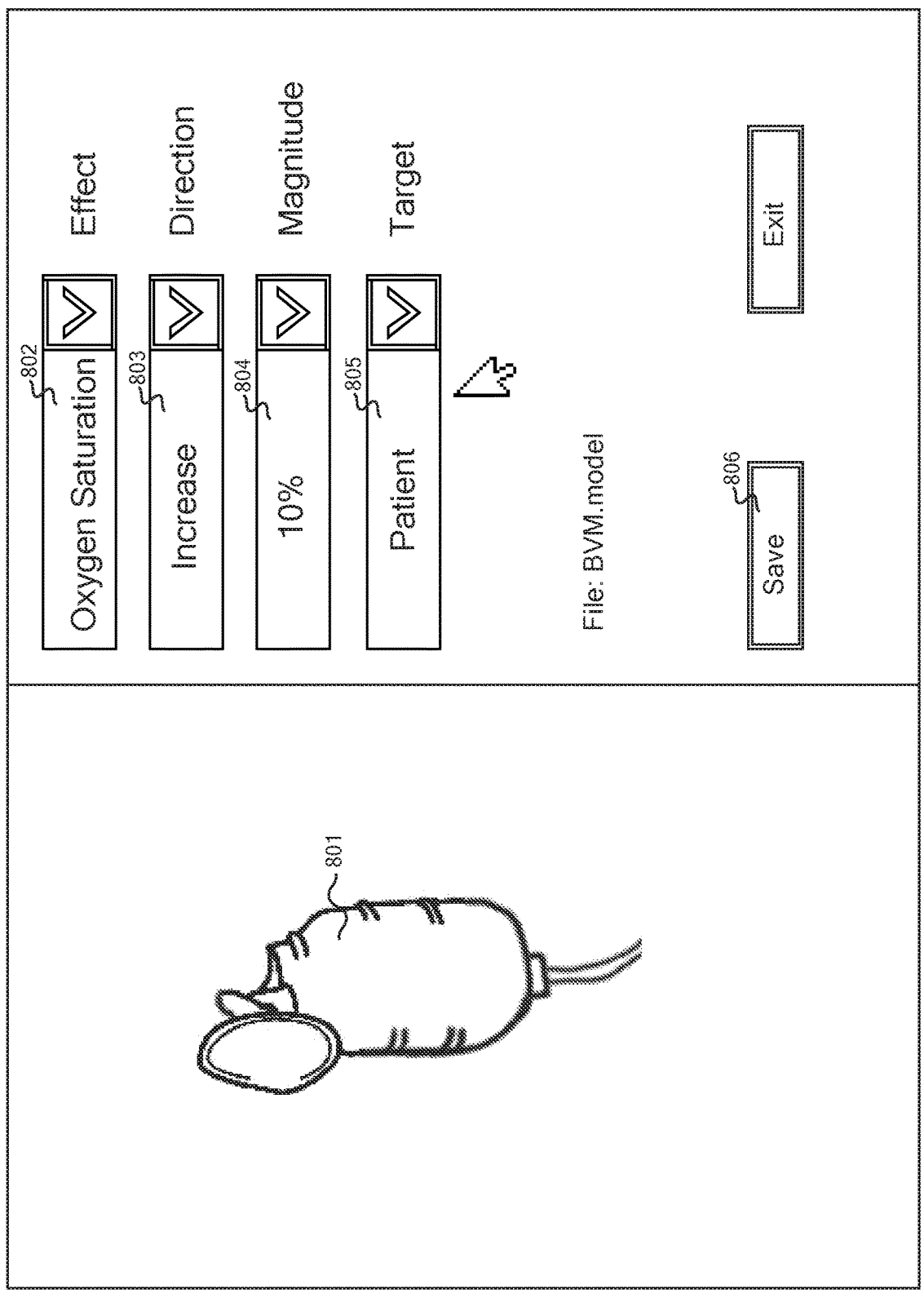
FIG. 8 is a diagram illustrating the use of software for the authoring of instruction files for a subcomponent tool for an augmented reality environment.

FIG. 8 shows one possible embodiment of an authoring program for instruction sets used by the augmented reality simulation system. In this embodiment, an author is creating an instruction set for use in a medical training simulation.

In this particular embodiment, the author is designing an instruction set for a particular tool, bag valve mask 801. The authoring program allows the specification of the appearance of the tool as well as its characteristics. In this example, the tool is used by participants on the virtual patient avatar, and the author is configuring the effects of the tool on the patient simulation. This includes the characteristic 802 that the tool affects, the direction 803 of the effect, the magnitude 804 of the effect, and the valid target 805 of the tool.

The instruction set can be saved using a save command 806. Saved tool instruction sets can then be loaded into other instruction sets for use in creating a simulation instruction set. The set can be saved locally, on a local database server, or it to an interne storage database for distribution. This database may be part of an instruction set marketplace, and other users may then be able to purchase licenses for use of the instruction set.

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

FIG. 9 is a block diagram that illustrates a computer system 900 upon which an embodiment of the invention may be implemented. Computer system 900 includes a bus 902 or other communication mechanism for communicating information, and a hardware processor 904 coupled with bus 902 for processing information. Hardware processor 904 may be, for example, a general purpose microprocessor.

Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Such instructions, when stored in non-transitory storage media accessible to processor 904, render computer system 900 into a special-purpose machine that is customized to perform the operations specified in the instructions.

Computer system 900 further includes a read only memory (ROM) 908 or other static storage device coupled to bus 902 for storing static information and instructions for processor 904. A storage device 910, such as a magnetic disk, optical disk, or solid-state drive is provided and coupled to bus 902 for storing information and instructions.

Computer system 900 may be coupled via bus 902 to a display 912, such as a cathode ray tube (CRT), for displaying information to a computer user. An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

Computer system 900 may implement the techniques described herein using customized hard-wired logic, one or more ASICs or FPGAs, firmware and/or program logic which in combination with the computer system causes or programs computer system 900 to be a special-purpose machine. According to one embodiment, the techniques herein are performed by computer system 900 in response to processor 904 executing one or more sequences of one or more instructions contained in main memory 906. Such instructions may be read into main memory 906 from another storage medium, such as storage device 910. Execution of the sequences of instructions contained in main memory 906 causes processor 904 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 910. Volatile media includes dynamic memory, such as main memory 906. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 902. Transmission media can also take the form of acoustic or light waves, such as those generated during radio-wave and infra-red data communications.

Various forms of media may be involved in carrying one or more sequences of one or more instructions to processor 904 for execution. For example, the instructions may initially be carried on a magnetic disk or solid-state drive of a remote computer. The remote computer can load the instructions into its dynamic memory and send the instructions over a telephone line using a modem. A modem local to computer system 900 can receive the data on the telephone line and use an infra-red transmitter to convert the data to an infra-red signal. An infra-red detector can receive the data carried in the infra-red signal and appropriate circuitry can place the data on bus 902. Bus 902 carries the data to main memory 906, from which processor 904 retrieves and executes the instructions. The instructions received by main memory 906 may optionally be stored on storage device 910 either before or after execution by processor 904.

Computer system 900 also includes a communication interface 918 coupled to bus 902. Communication interface 918 provides a two-way data communication coupling to a network link 920 that is connected to a local network 922. For example, communication interface 918 may be an integrated services digital network (ISDN) card, cable modem, satellite modem, or a modem to provide a data communication connection to a corresponding type of telephone line. As another example, communication interface 918 may be a local area network (LAN) card to provide a data communication connection to a compatible LAN. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams. The signals through the various networks and the signals on network link 920 and through communication interface 918, which carry the digital data to and from computer system 900, are example forms of transmission media.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918.

The received code may be executed by processor 904 as it is received, and/or stored in storage device 910, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A method comprising:
    receiving, by an authoring application running on a computing device, a set of one or more values that define at least one of a physical or a physiological property of a virtual avatar;
    in response to receiving the set of one more values, generating, by the authoring application running on the computing device, an instruction set for virtual avatar projection into an augmented or virtual reality environment;
    wherein the instruction set includes instructions used by an augmented or virtual reality application to project the virtual avatar into real or virtual space such that the virtual avatar exhibits a behavior based, at least in part, on at least one of the physical or the physiological properties defined through the authoring application;
    executing the instruction set by the augmented or virtual reality application for a plurality of augmented or virtual reality devices, wherein each respective augmented or virtual reality device of the plurality of augmented or virtual reality devices concurrently projects a respective view from a different angle of the virtual avatar exhibiting the behavior based on a physical location of the respective augmented or virtual reality device;
    detecting, by a wireless sensor of at least one of the augmented or virtual reality devices of the plurality of virtual reality devices, an interaction between a medical tool that is or virtually present in the real or virtual space and the virtual avatar;
    simulating, within the respective view for each respective augmented or virtual reality device, a physiological response based at least in part on a type of medical tool being used in the interaction and at least one of the physical or the physiological properties defined through the authoring application.

2. The method according to claim 1, wherein the instruction set generated by the authoring application is operable to trigger changes to the augmented or virtual reality environment over time or based upon a passage of time, such that a sequence of events occurs in the augmented or virtual reality environment as defined by the instruction set.

3. The method according to claim 2, wherein a sequence of events occurring over time and defined by an instruction set is operable to be navigated by pausing execution, reversing execution, accelerating execution, moving to any time point in the instruction set and starting execution from that point, resuming execution, or stopping execution for all participants sharing the augmented or virtual reality environment.

4. The method according to claim 1, wherein generating the instruction set comprises selecting from a set of predefined instructions, composing new instructions, or uploading instructions from an external piece of non-transitory computer readable media.

5. The method according to claim 1, wherein the authoring application allows for an author to allow at least one characteristic of at least one virtual avatar to change in response to any change in the augmented or virtual reality environment.

6. The method according to claim 1, wherein the instruction set generated by the authoring application is distributed to other users via an online marketplace, allowing for control of access to the instruction set, charging of fees for the instruction set, or collection of data regarding usage of the instruction set.

7. The method according to claim 1, wherein the instruction set generated by the authoring application causes the behavior is a physiological reaction that is exhibited responsive to interactions taken by a participant of the augmented or virtual reality environment during simulation of a medical procedure.

8. The method of claim 1, wherein the augmented or virtual reality application broadcasts, via a router, information for projecting views of the virtual avatar to the plurality of augmented or virtual reality devices based on respective physical locations of the plurality of augmented or virtual reality devices.

9. The method of claim 8, wherein at least two of the plurality of augmented or virtual reality devices are being used at different physical locations but allow users to walk around and interact with projections of the virtual avatar as if occupying a shared physical space.

10. The method of claim 1, wherein the instructions further cause operations comprising:
receiving, by the augmented or virtual reality application from a moderator, a modification to a current medical state of the virtual avatar;
responsive to receiving the modification, updating views of the virtual avatar that are projected by the plurality of augmented or virtual reality devices.

11. One or more non-transitory computer-readable media storing instructions which, when executed by one or more computing devices, causes operations comprising:
receiving, by an authoring application running on a computing device, a set of one or more values that define at least one of a physical or a physiological property of a virtual avatar;
in response to receiving the set of one more values, generating, by the authoring application running on the computing device, an instruction set for virtual avatar projection into an augmented or virtual reality environment;
wherein the instruction set includes instructions used by an augmented or virtual reality application to project the virtual avatar into real or virtual space such that the virtual avatar exhibits a behavior based, at least in part, on at least one of the physical or the physiological properties defined through the authoring application;
executing the instruction set by the augmented or virtual reality application for a plurality of augmented or virtual reality devices, wherein each respective augmented or virtual reality device of the plurality of augmented or virtual reality devices concurrently projects a respective view from a different angle of the virtual avatar exhibiting the behavior based on a physical location of the respective augmented or virtual reality device;
detecting, by a wireless sensor of at least one of the augmented or virtual reality devices of the plurality of virtual reality devices, an interaction between a medical tool that is present in the real or virtual space and the virtual avatar;
simulating, within the respective view for each respective augmented or virtual reality device, a physiological response based at least in part on a type of medical tool being used in the interaction and at least one of the physical or the physiological properties defined through the authoring application.

12. The one or more non-transitory computer-readable media of claim 11, wherein the instruction set generated by the authoring application is operable to trigger changes to the augmented or virtual reality environment over time or based upon a passage of time, such that a sequence of events occurs in the augmented or virtual reality environment as defined by the instruction set.

13. The one or more non-transitory computer-readable media of claim 12, wherein a sequence of events occurring over time and defined by an instruction set is operable to be navigated by pausing execution, reversing execution, accelerating execution, moving to any time point in the instruction set and starting execution from that point, resuming execution, or stopping execution for all participants sharing the augmented or virtual reality environment.

14. The one or more non-transitory computer-readable media of claim 11, wherein generating the instruction set comprises selecting from a set of predefined instructions, composing new instructions, or uploading instructions from an external piece of non-transitory computer readable media.

15. The one or more non-transitory computer-readable media of claim 11, wherein the authoring application allows for an author to allow at least one characteristic of at least one virtual avatar to change in response to any change in the augmented or virtual reality environment.

16. The one or more non-transitory computer-readable media of claim 11, wherein the instruction set generated by the authoring application can be is distributed to other users via an online marketplace, allowing for control of access to the instruction set, charging of fees for the instruction set, or collection of data regarding usage of the instruction set.

17. The one or more non-transitory computer-readable media of claim 11, wherein the instruction set generated by the authoring application causes the behavior is a physiological reaction that is exhibited responsive to interactions taken by a participant of the augmented or virtual reality environment during simulation of a medical procedure.

18. The one or more non-transitory computer-readable media of claim 11, wherein the augmented or virtual reality application broadcasts, via a router, information for projecting views of the virtual avatar to the plurality of augmented or virtual reality devices based on respective physical locations of the plurality of augmented or virtual reality devices.

19. The one or more non-transitory computer-readable media of claim 18, wherein at least two of the plurality of augmented or virtual reality devices are being used at different physical locations but allow users to walk around and interact with projections of the virtual avatar as if occupying a shared physical space.

20. The one or more non-transitory computer-readable media of claim 11, wherein the instructions further cause operations comprising:
    receiving, by the augmented or virtual reality application from a moderator a modification to a current medical state of the virtual avatar;
    responsive to receiving the modification, updating views of the virtual avatar that are projected by the plurality of augmented or virtual reality devices.

\* \* \* \* \*